(12) United States Patent
Testud et al.

(10) Patent No.: US 6,334,363 B1
(45) Date of Patent: Jan. 1, 2002

(54) DEVICE FOR MEASURING PRESSURE POINTS TO BE APPLIED BY A COMPRESSIVE ORTHOTIC DEVICE

(75) Inventors: Jean-Louis Testud, Paris; Mohammed Sennoune, Evreux; Jean-Pierre Prudhomme, Antony; Amina Ouchene, Maisons Alfort, all of (FR)

(73) Assignee: Innothera Topic International, Arcueil (FR)

( * ) Notice: Subject to any disclaimer, the term of this patent is extended or adjusted under 35 U.S.C. 154(b) by 0 days.

(21) Appl. No.: 09/446,709
(22) PCT Filed: Jun. 23, 1998
(86) PCT No.: PCT/FR98/01322
  § 371 Date: May 25, 2000
  § 102(e) Date: May 25, 2000
(87) PCT Pub. No.: WO98/58605
  PCT Pub. Date: Dec. 30, 1998

(30) Foreign Application Priority Data
Jun. 23, 1997 (FR) ............................................. 97 07787

(51) Int. Cl.$^7$ .................................................. G01D 7/00
(52) U.S. Cl. .................................... 73/862.046; 73/772
(58) Field of Search .................. 73/790, 772, 862.041, 73/862.042, 862.043, 862.044, 862.045, 862.046

(56) References Cited

U.S. PATENT DOCUMENTS

| | | |
|---|---|---|
| 3,818,756 A | 6/1974 | Barron et al. |
| 4,137,763 A | 2/1979 | Swallow |
| 4,417,401 A | 11/1983 | Aisaka et al. |
| 4,584,625 A | 4/1986 | Kellogg |
| 4,858,620 A * | 8/1989 | Sugarman et al. .......... 128/774 |
| 5,253,656 A * | 10/1993 | Rincoe et al. .............. 128/782 |
| 5,976,099 A * | 11/1999 | Kellogg ........................ 602/23 |
| 6,106,463 A * | 8/2000 | Wilk .......................... 600/437 |

FOREIGN PATENT DOCUMENTS

EP  0 088 860  9/1983

\* cited by examiner

*Primary Examiner*—Max Noori
(74) *Attorney, Agent, or Firm*—Nixon & Vanderhye P.C.

(57) ABSTRACT

The device comprises a rigid former reproducing the volume of a portion of the body and suitable for receiving the compressive orthosis. The former (10) incorporates a plurality of sensors (22) distributed over various points of the former and configured in such a manner as to avoid significantly modifying the surface profile of the former, the sensors essentially measuring the pressure applied locally on the former by the orthosis at the location of the sensor and perpendicularly to the surface of the former. Advantageously, at the location of the measurement point, each sensor comprises a thin wall capable of being subjected to microdeformation under the effect of the pressure applied by the orthosis, and means such as a strain gauge bridge, for example. The thin wall can constitute a portion of a support pellet which is fitted to the former in such a manner that its outside surface, which includes the thin wall, is flush with the outside surface of the former.

6 Claims, 2 Drawing Sheets

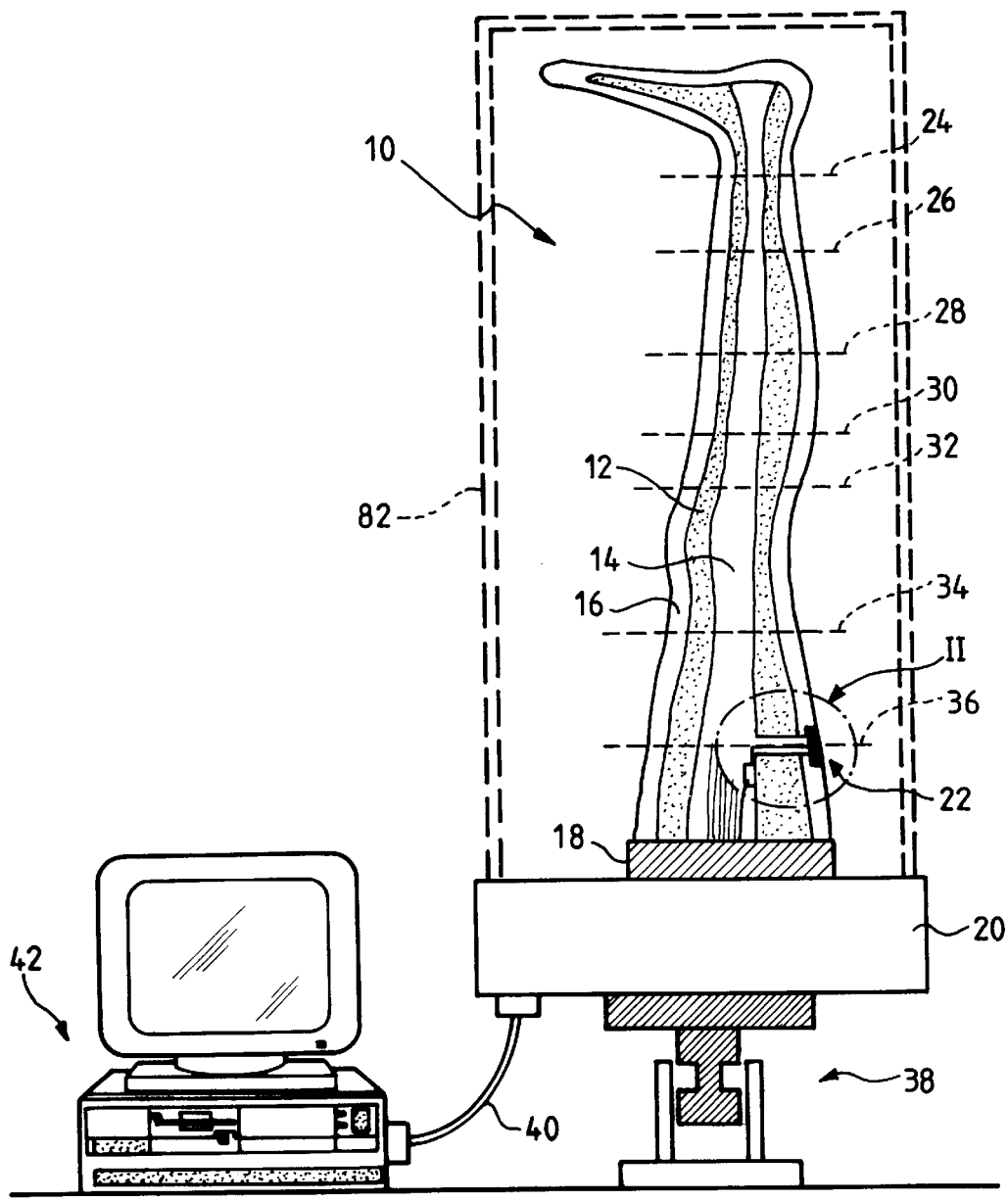
FIG_1

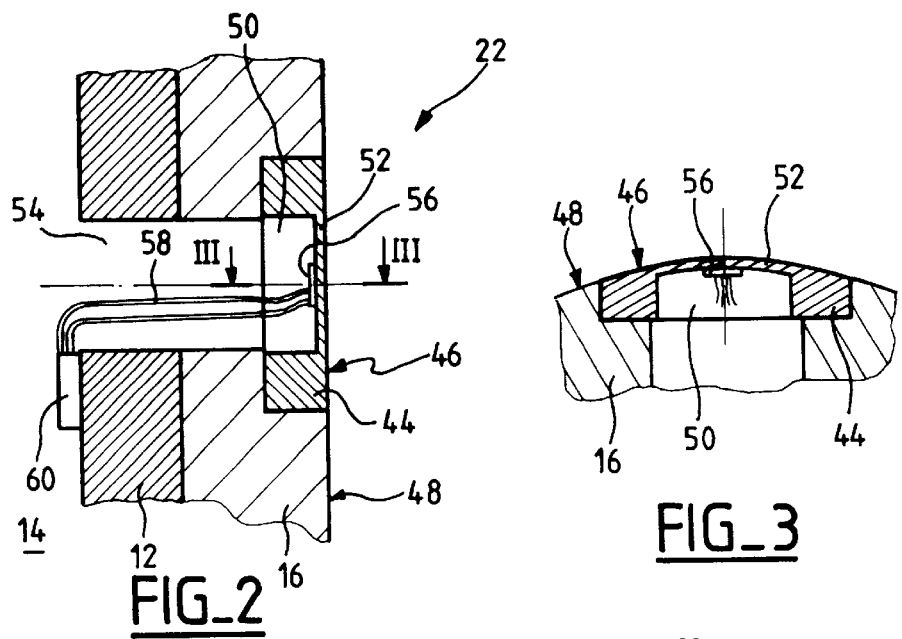
FIG_2
FIG_3
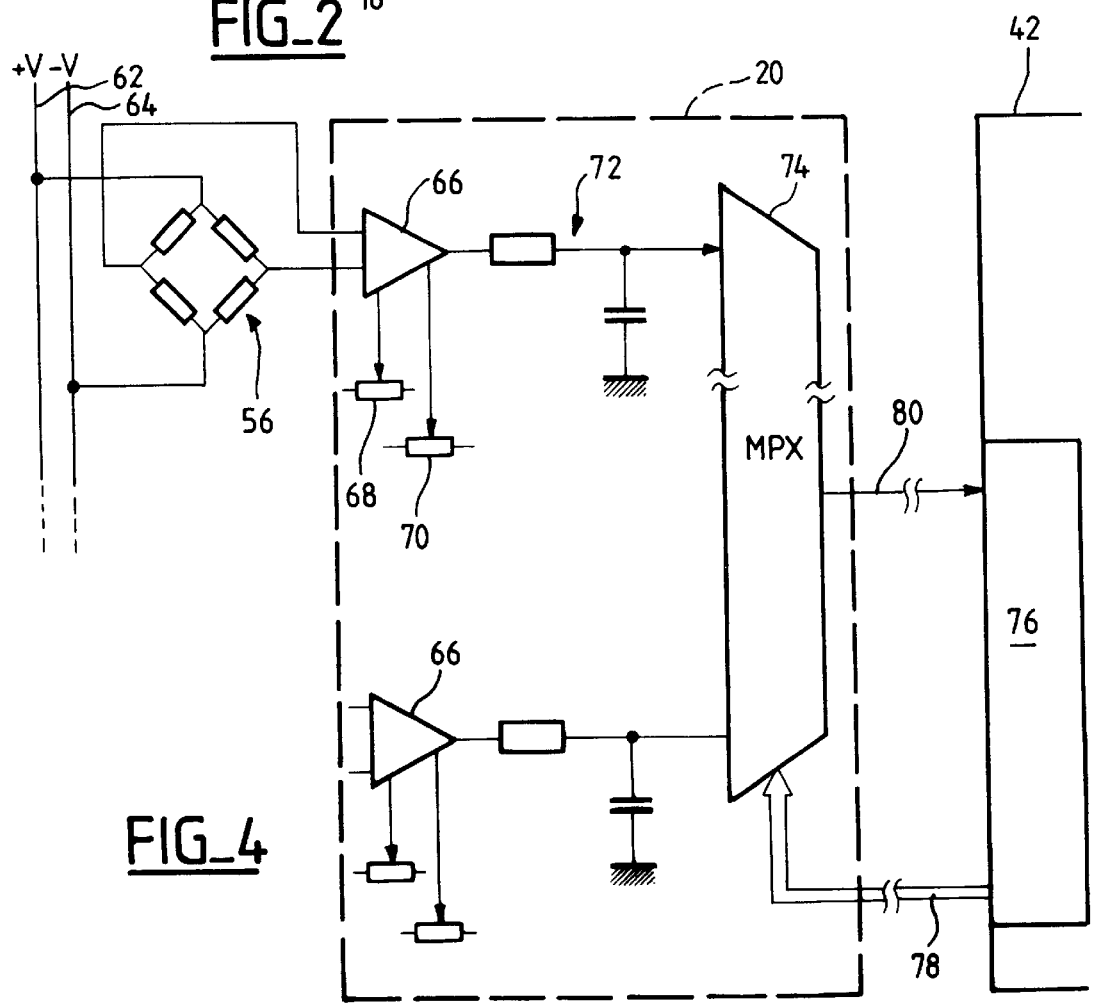
FIG_4

DEVICE FOR MEASURING PRESSURE POINTS TO BE APPLIED BY A COMPRESSIVE ORTHOTIC DEVICE

BACKGROUND OF THE INVENTION

1. Field of the Invention

The invention relates to measuring the restraining pressures that a compressive orthosis serves to apply on a portion of the body.

2. Discussion of Prior Art

The invention is more particularly described for the case where the portion of the body in question is the leg and the compressive orthosis is an elastic stocking. Nevertheless, the invention is not limited to that particular case and it applies to other types of orthosis and/or to other portions of the body, for example elastic strips for application to the leg or to a portion of the leg, a belt for applying pressure to the abdomen, etc.

The pressures exerted by such orthoses are small, of the order of 0 to 100 hPa, and typically of the order of 20 hPa to 70 hPa, in relative pressure terms.

Numerous factors can influence the value of this pressure and can give rise to differences from a standard nominal value, e.g. knitting machine adjustments, manufacturing tolerances, processing such as dying the stockings, etc.

It is therefore necessary to be able to measure accurately and reproducibly the pressure that is really applied by a given compressive orthosis, in particular to verify that complies with nominal values (quality control during manufacture).

Until now, such measurement has been performed by placing the stocking that is to be inspected on a wooden jig or "tree" of standardized shape and dimensions ("Hohenstein model", sizes 1, 2, 3, or 4), and by sliding a thin rubber capsule between the stocking and the tree, which capsule constitutes a pressure sensor (a device known as a "Compritest"), and by noting the pressure given by the capsule, firstly without the stocking, and then with the stocking. The desired value is obtained by taking the difference between those two values.

Nevertheless, that method suffers from three major drawbacks:

firstly, its accuracy is poor given that firstly the pressure applied by the stocking is relatively small compared with the sensitivity of the pressure gauge capsule, and secondly because placing the sensor between the stocking and the tree changes the tension of the stocking specifically at the location where the measurement is being performed, thus falsifying the measurement;

measurement is difficult and highly dependent on the skill of the operator since it is necessary to slide the capsule between the stocking and the tree while moving the stocking as little as possible: it is thus difficult to ensure that the method is reproducible; and finally, that method gives local measurements only and in order to obtain another measurement point it is necessary to repeat the operation (putting the capsule into place) as many times as there are desired measurement points.

SUMMARY OF THE INVENTION

An object of the invention is to remedy those drawbacks, by proposing a device that makes it possible to draw up a genuine map of the pressures that can be applied by a compressive orthosis on a portion of the body, and having the following advantages:

the measurement is accurate;

the measurement is faithful in that it provides data in a manner that is reproducible and independent of the skill of an operator;

measurements are performed on a large number of points simultaneously (or quasi-simultaneously if multiplexing is used, for example), thereby obtaining an anatomically representative grid for the map of pressures applied by the compressive orthosis;

it can be implemented simply and quickly; and the various data measurements taken can be digitized, stored, processed, and displayed, in particular for the purpose of interfacing with computer processing.

To this end, the device of the invention which presents a rigid former reproducing the volume of the portion of the body under investigation and suitable for receiving the compressive orthosis is characterized in that the former incorporates a plurality of sensors distributed over different points of the former and configured in such a manner as to avoid significantly modifying the surface profile thereof, and in that said sensors essentially measure the pressure that is applied locally to the former by the orthosis at the location of the sensor and perpendicularly to the surface of the former.

According to a certain number of advantageous features:

the sensors comprise, at each measurement point, a thin wall capable of being subjected to microdeformation under the effect of the pressure applied by the orthosis, and measurement means, in particular a temperature-compensated strain gauge bridge, for measuring said microdeformation;

the thin wall forms a portion of a support pellet fitted to the former in such a manner that its outside surface, which includes the thin wall, is flush with the surface of the former;

the device further comprises means for calibrating the sensors by means of a leakproof enclosure that can be pressurized and that encloses the former; and the device further comprises means for processing and displaying the measurements taken by the sensors.

BRIEF DESCRIPTION OF THE DRAWINGS

An embodiment of the invention is described below with reference to the accompanying figures.

FIG. 1 is a diagrammatic partially-cutaway elevation view of the device of the invention connected to a computer for making use of the measured data.

FIG. 2 is a view on a larger scale of the detail marked II in FIG. 1, showing the structure of one of the sensors of the device.

FIG. 3 is a section view on III—III of FIG. 2.

FIG. 4 is a block diagram showing the electronic circuits for processing the measurement signals supplied by the sensors of the device of the invention.

DETAILED DISCUSSION OF PREFERRED EMBODIMENTS

In FIG. 1, reference 10 designates overall a rigid former that is representative of a limb (or more generally of a portion of the body) on which compression is to be applied. In the example shown, it is constituted by a leg former having dimensions corresponding to one of the four sizes 1 to 4 of the standardized "Hohenstein model".

The former 10 has a central core 12 or "salmon" made of metal having a hollow center so as to provide an access tunnel 14 serving specifically to pass and keep together the wires connected to the various sensors (see below). The metal "salmon" 12 is covered in a covering 16, e.g. of epoxy resin, that is molded to have the same dimensions as the standardized jig or tree. The surface state of the covering 16 is made to be smooth and without roughnesses so as to make it easy to put an elastic stocking into place in uniform manner on the former 10.

Advantageously, e.g. to make it possible to exchange a faulty sensor or to verify the interconnections, the former is made up of a plurality of separable elements that are assembled together in leakproof manner without gaps, e.g. five independent elements respectively representing a "thigh", a "knee", a "calf", an "ankle" and a "foot".

The entire former is placed on a support ring 18 which is itself mounted on a box 20 that may, in particular, contain the electronics for processing the signals.

The former 10 is provided with a plurality of sensors 22 which are described in greater detail with reference to FIGS. 2 and 3, the sensors being placed at various successive levels up the leg, e.g. at seven successive levels 24 to 36, with each level having five to eleven sensors distributed around its periphery. The distribution of the sensors can be as indicated in the table below, giving a total of sixty sensors, i.e. sixty simultaneous pressure measurements at seven levels along the leg (with "height above ground" corresponding to the height of the sensor measured in the proximal direction from the sole of the foot).

| Level No. | Height above ground (cm) | No. of sensors per level | Angle between sensors (°) | Corresponding linear spacing (cm) |
|---|---|---|---|---|
| 1 | 12 | 5 | 72 | 4.6 |
| 2 | 20 | 6 | 60 | 4.8 |
| 3 | 31 | 8 | 45 | 4.4 |
| 4 | 39 | 8 | 45 | 4.3 |
| 5 | 45 | 11 | 32.7 | 3.4 |
| 6 | 60 | 11 | 32.7 | 4.3 |
| 7 | 72 | 11 | 32.7 | 4.7 |

The assembly can be mounted on a rotary support 38 of the same type as that used with traditional Hohenstein jigs to make it easy to put on the stocking.

The electronic unit 20 is connected by a link 40 to a microcomputer 42 that performs signal processing and that displays the measured pressures.

The structure of the sensors is described in greater detail with reference to FIGS. 2 and 3. FIG. 2 is a section in elevation through one of the sensors 22, and FIG. 3 is a plan view, in section, through the same sensor, showing the curvature of the leg.

The sensor 22 is made from a support pellet 44, e.g. made of epoxy resin, whose outside surface 46 is defined in such a manner as to present locally the same curvature as the remainder of the leg and so as to ensure that there are no gaps relative to the outside surface 48 thereof. Thus, the shape has no projections or discontinuities in the vicinity of a sensor, and therefore does not get in the way of putting the stocking on the former, and above all does not modify in any way the conditions under which pressure is applied to the leg by the stocking (unlike the prior art device in which a capsule is interposed between the stocking and the jig, thereby locally modifying the conditions with which compression is applied).

Internally, the pellet 44 has a cavity 50 so as to define a thin wall or membrane 52 between said cavity and the outside surface 46, which wall or membrane is capable of being subjected to microdeformation. The term "microdeformation" is used herein to mean a change of curvature that is large enough to be measurable but small enough to avoid significantly modifying on a macroscopic scale the local conditions with which pressure is applied by the stocking to the measurement point.

Typical dimensions for a support pellet 44 are as follows: outside diameter =24 mm; inside diameter of the cavity 50=13 mm; thickness of the diaphragm 52=0.75 mm; and radius of curvature of the surface 46=36 mm to 80.5 mm depending on the location of the sensor. To measure the microdeformation of the wall 52, a strain gauge 56 is stuck thereon inside the cavity 50, e.g. a bridge having four strain gauges of the kind that is suitable for measuring pressure by means of a diaphragm and that is temperature compensated.

The power supply and measurement wires 58 of the strain gauge 56 pass through the covering 16 and the metal "salmon" 12 via a strain gauge well 54 that opens out into the access tunnel 14 and that enables the wires to be connected to a primary connector 60, itself connected to the electronic unit 20 as are other corresponding connectors.

FIG. 4 shows the electronics circuits that enable measurement to be performed: one of the diagonals of the strain gauge bridge 56 is fed with two symmetrical voltages 62 and 64 while the other diagonal is connected to two inputs of a differential amplifier 66, and the gain and the offset of each amplifier can be adjusted individually by means of respective potentiometers 68 and 70. The output signal from the amplifier 66 is transmitted via a lowpass filter 72 to an analog multiplexer 74 whose inputs receive the signals delivered by the various amplifiers associated with the strain gauges of each of the sixty sensors in question. The output signal from the multiplexer 74 is applied to the input of an analog card 76 of the microcomputer 42 which addresses the multiplexer 74 via a bus 78 so as to cause it to supply a line 80 with one of the sixty measurement signals coming from the sensors.

The sensors are scanned cyclically and continuously, thereby making it possible simultaneously to provide a varying display of all of the pressure values observed at the various measurement points.

These values can be displayed in digital form (value of the relative pressure in hPa), and also in graphical form, e.g. using a bar chart and/or a colored graphic, where color varies relative to the reference pressure for the measurement point under consideration (e.g. green if the pressure differs by no more than a predetermined amount from the reference value, and red otherwise).

The measured values can also be subjected to various mathematical processes, for example a mathematical model can be applied in which parameter values are determined for each measurement point for the purpose of compensating local effects such as the thicknesses of the sensitive walls which depend on the radius of curvature of the former at the corresponding location.

In order to adjust the individual gain and offset parameters for each of the amplifiers 66, an initial step is provided in which the sensors are calibrated, which step is performed by putting the entire device in an enclosure 82 (FIG. 1) and then putting said enclosure under accurately calibrated pressure: adjustments are then performed until all of the sensors display the same pressure value: zero pressure when the enclosure 82 is absent, and calibration pressure after the enclosure 82 has been pressurized.

This adjustment can be performed in various ways: the gain and offset potentiometers can be adjusted manually, the gains and the offsets can be adjusted under program control from the microcomputer, or indeed by choosing amplifiers that avoid the need for compensation.

The invention has numerous applications, amongst which the following can be mentioned:

- in a factory, adjusting knitting machines and performing production quality control;
- in a clinic, as an analysis tool for verifying that the compression actually applied by the orthosis confirms with the compression prescribed by the practitioner, or for dynamically studying pressure variations as a function of movements of the limb (in which case the former needs to be jointed);
- in the field of teaching for training in the technique of putting compression strips into place: by displaying pressures immediately, it is possible immediately while the strip is being put into place to see whether the tension of the strip is too little or too much; and
- in the military field for evaluating the effectiveness of "anti-g" suits which apply pressures in controlled manner to certain portions of the bodies of fighter pilots in order to compensate for the high accelerations to which they can be subjected in flight.

What is claimed is:

1. A device for establishing a simultaneous map of pressures applied by a compressive orthosis on a portion of the body, said device comprising:

a rigid former reproducing the volume of said body portion and suitable for receiving the compressive orthosis, a plurality of embedded sensors (22) distributed over different points of the former and configured in such a manner as to avoid significantly modifying the surface profile thereof, said sensors essentially measure the pressure that is applied locally to the former by the orthosis at the location of the sensor and perpendicularly to the surface of the former.

2. The device of claim 1, in which the sensors comprise, at each measurement point, a thin wall (52) capable of being subjected to microdeformation under the effect of the pressure applied by the orthosis, and means for measuring said microdeformation.

3. The device of claim 2, in which the means for measuring the microdeformation of the thin wall comprise a temperature-compensated strain gauge bridge (56).

4. The device of claim 2, in which the thin wall forms a portion of a support pellet (44) fitted to the former in such a manner that its outside surface (46), which includes the thin wall, is flush with the surface (48) of the former.

5. The device of claim 2, further comprising means for calibrating the sensors by means of a leakproof enclosure (82) capable of being pressurized and that encloses the former.

6. The device of claim 1, further comprising means (20, 42) for processing and displaying the measurements taken by the sensors.

* * * * *